(12) United States Patent
Bailey (10) Patent No.: US 7,160,280 B2
(45) Date of Patent: Jan. 9, 2007

(54) DIAPER WITH SEGREGATED RESERVOIR

(76) Inventor: Brenda Lee Bailey, 420 Churchwell Dr., Panama City Beach, FL (US) 32407

( * ) Notice: Subject to any disclaimer, the term of this patent is extended or adjusted under 35 U.S.C. 154(b) by 137 days.

(21) Appl. No.: 10/779,451

(22) Filed: Feb. 13, 2004

(65) Prior Publication Data

US 2005/0182382 A1  Aug. 18, 2005

(51) Int. Cl.
A61F 13/15 (2006.01)
A61F 5/44 (2006.01)
(52) U.S. Cl. .................. 604/385.19; 604/348; 604/355
(58) Field of Classification Search ........... 604/385.01, 604/385.19, 385.31, 348, 355, 378, 385.09; 4/144.1, 144.2, 144.3, 144.4; D24/122, 123, D24/124, 126
See application file for complete search history.

(56) References Cited

U.S. PATENT DOCUMENTS

| 5,520,674 | A | * | 5/1996 | Lavon et al. ........... 604/385.16 |
| 5,643,241 | A | * | 7/1997 | Ahr et al. ............... 604/385.12 |
| 6,022,338 | A | * | 2/2000 | Putzer .................... 604/385.01 |
| 6,133,501 | A |   | 10/2000 | Hallock et al. |
| 6,168,584 | B1 | * | 1/2001 | Allen et al. ............. 604/385.19 |
| 6,328,724 | B1 | * | 12/2001 | Ronnberg et al. ...... 604/385.24 |
| 6,346,097 | B1 |   | 2/2002 | Blaney |
| 6,383,170 | B1 |   | 5/2002 | Mishima et al. |
| 6,395,955 | B1 | * | 5/2002 | Roe et al. .................... 604/361 |
| 6,409,715 | B1 |   | 6/2002 | Tanji |
| 6,458,110 | B1 | * | 10/2002 | Lavon et al. .......... 604/385.01 |
| 6,458,144 | B1 |   | 10/2002 | Morris et al. |
| 6,464,676 | B1 |   | 10/2002 | Mishima |
| 6,468,256 | B1 |   | 10/2002 | Mishima |
| 6,471,681 | B1 | * | 10/2002 | Ronnberg et al. ...... 604/385.19 |
| 6,527,756 | B1 |   | 3/2003 | Mishima et al. |
| 6,595,972 | B1 | * | 7/2003 | Wise et al. ............ 604/385.01 |
| 6,595,975 | B1 | * | 7/2003 | Vogt et al. ............. 604/385.19 |
| 6,716,204 | B1 | * | 4/2004 | D'Acchioli et al. ... 604/385.19 |
| 6,840,926 | B1 | * | 1/2005 | Nukina et al. ......... 604/385.03 |
| 6,932,800 | B1 | * | 8/2005 | LaVon et al. .......... 604/385.14 |
| 2003/0045853 | A1 | * | 3/2003 | Sauer .................... 604/385.19 |
| 2004/0193130 | A1 | * | 9/2004 | Fima et al. ............ 604/385.01 |

* cited by examiner

Primary Examiner—Jacqueline Stephens
Assistant Examiner—Michael G. Bogart
(74) Attorney, Agent, or Firm—John Wiley Horton (57) ABSTRACT

A diaper with an integral feces receiver. This receiver is connected to the interior of the diaper by an oval opening. The walls of the receiver are undercut so that the cross-section expands as the fecal matter moves from the opening downward. A thickened supporting section is provided around the receiver so that the user's weight will not force the solid material out of the receiver and back into the interior of the diaper. The fecal matter is thereby contained within the receiver and away from the user. A layered version is shown, in which the diaper's structure is built from a series of stacked cross sections.

12 Claims, 9 Drawing Sheets

FIG. 8

DIAPER WITH SEGREGATED RESERVOIR

CROSS-REFERENCES TO RELATED APPLICATIONS

Not Applicable.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to the field of diapers. More specifically, the invention comprises a diaper including a segregated feces receiver.

2. Description of the Related Art

Disposable diapers have been in common use for many years. These typically employ a layer of absorbent material enclosed within a moisture-proof barrier layer. The traditional solution to accommodating additional fluid and solid matter has been to increase the thickness of the absorbent layer. However, this approach does not work well for adult diapers.

Feces containment is a significant concern in the field of adult diapers. Because such a large volume of solid may be produced, it is difficult to contain this mass within the diaper without also causing significant exposure to the user's skin. As those skilled in the art will know, significant exposure of the skin to fecal matter can cause problems. Thus, it is desirable to provide a diaper which can contain a significant quantity of fecal matter without exposing the wearer's skin to the fecal matter.

BRIEF SUMMARY OF THE PRESENT INVENTION

The present invention comprises a diaper with an integral feces receiver. This receiver is connected to the interior of the diaper by an opening. The walls of the receiver are undercut so that the cross-section expands as the fecal matter moves from the opening downward. A thickened supporting section is provided around the receiver so that the user's weight will not force the solid material out of the receiver and back into the interior of the diaper. The fecal matter is thereby contained within the receiver and away from the user. A layered version is shown, in which the diaper's structure is built from a series of stacked cross sections.

REFERENCE NUMERALS IN THE DRAWINGS

| 10 | diaper | 12 | leg relief |
|---|---|---|---|
| 14 | feces receiver | 18 | adhesive strip |
| 20 | front belt | 22 | rear belt |
| 24 | center portion | 26 | front wing |
| 28 | rear wing | 30 | hem |
| 32 | opening | 34 | undercut |
| 36 | bottom wall | 38 | support |
| 40 | laminated diaper | 42 | sealing layer |
| 44 | first absorbent layer | 46 | second absorbent layer |
| 48 | third absorbent layer | 50 | fourth absorbent layer |
| 52 | fifth absorbent layer | 54 | first opening |
| 56 | second opening | 57 | third opening |
| 58 | fourth opening | 60 | fifth opening |
| 62 | interior | 64 | side wall |
| 66 | lower layer | 68 | sixth opening |
| 70 | front edge | 72 | back edge |

DETAILED DESCRIPTION OF THE INVENTION

Figure 1:
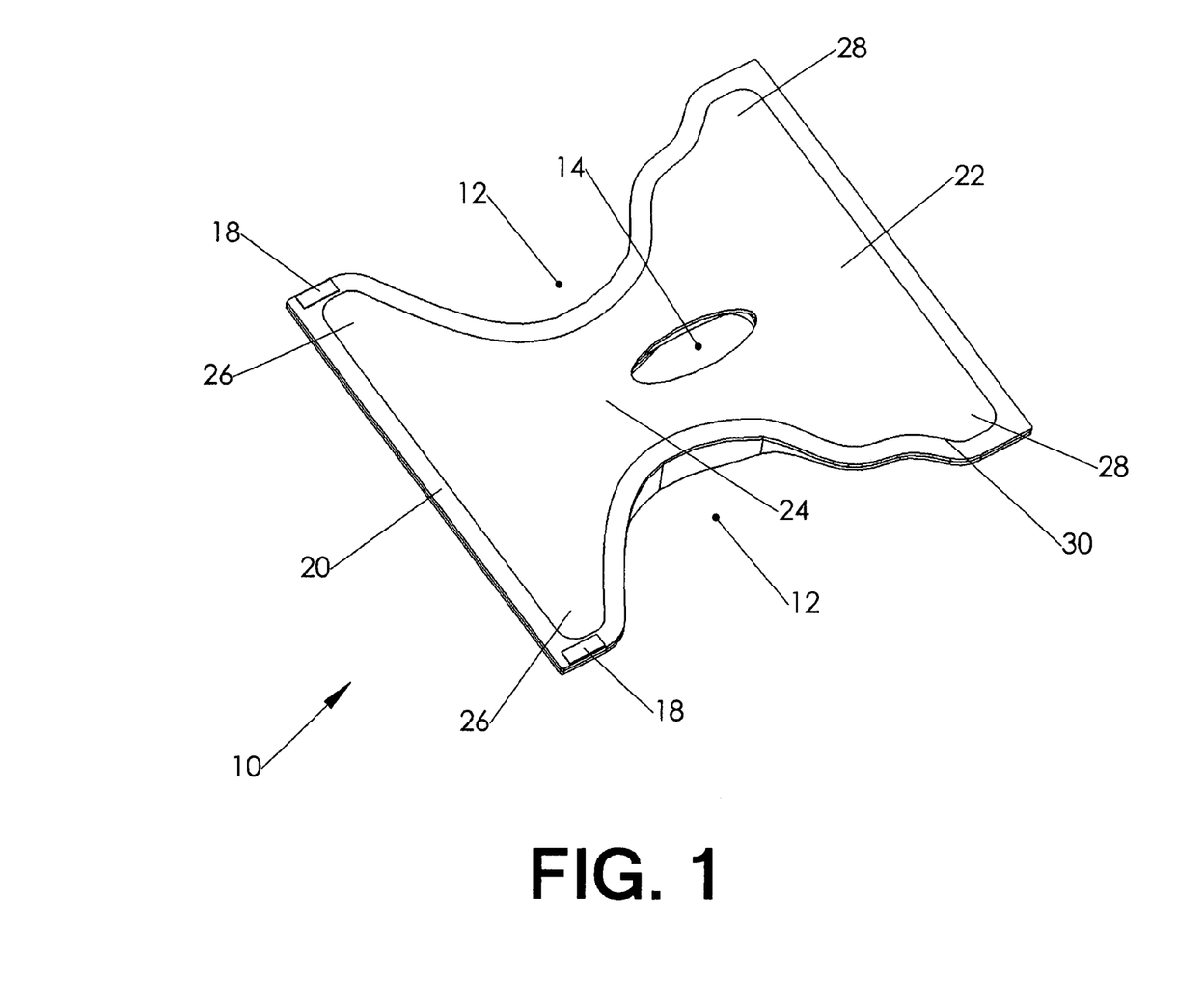
FIG. 1 is an isometric view, showing the present invention.

FIG. 1 shows the present invention in its uninstalled state (lying flat). Diaper 10 is comprised of center portion 24 joined to rear belt 22 and front belt 20. The combination of these three portions forms an hourglass shape. Two leg reliefs 12 are included. Two rear wings 28 are located on either end of rear belt 22. Likewise, two front wings 26 are located on either end of front belt 20. Closure means are typically provided proximate these front wings and rear wings. Commonly used closure means include hook and loop patches (VELCRO), adhesive strips, snaps, and the like. In order to provide additional accommodation for varying sizes an elastic portion can be included in the front belt or the rear belt.

Figure 2:
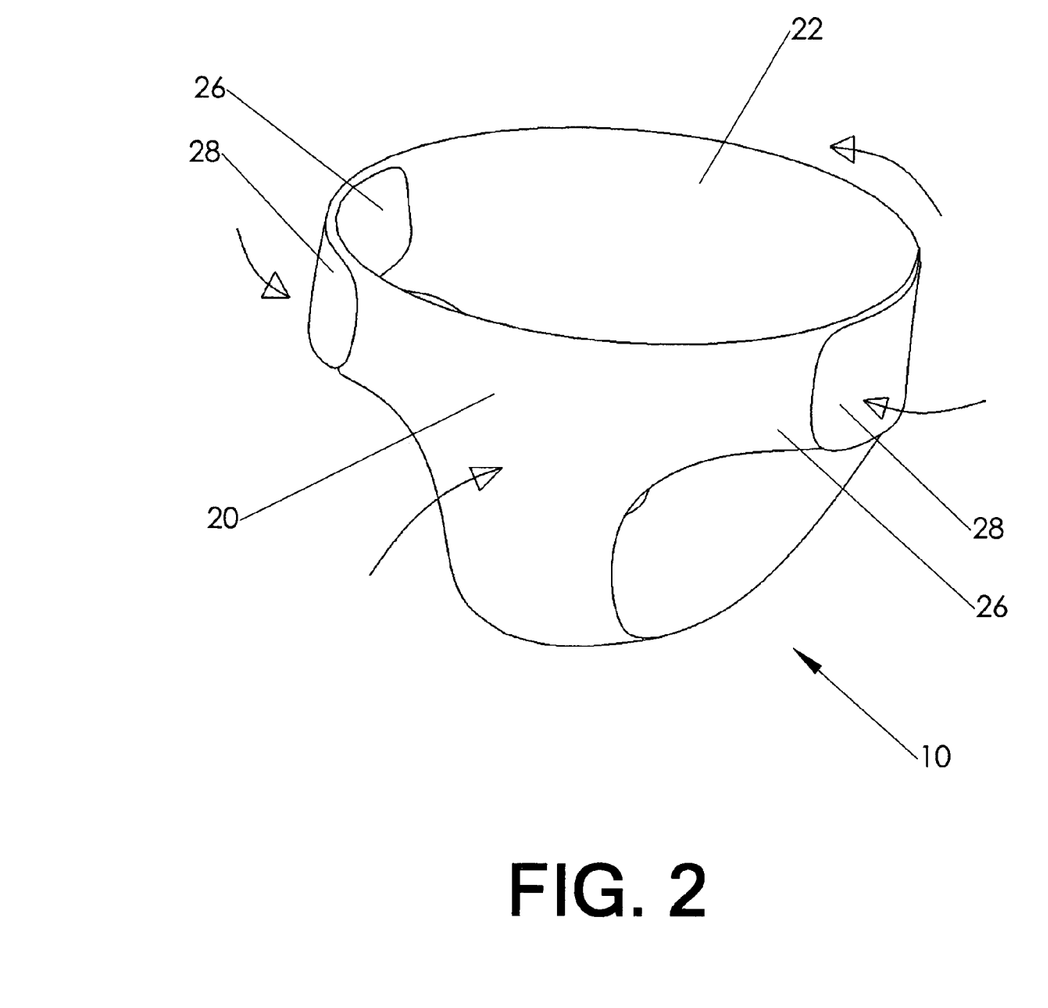
FIG. 2 is an isometric view, showing the present invention as it would be worn by a user.

Turning briefly to FIG. 2, diaper 10 is shown folded into its installed state (as it would typically be worn by a user). Each rear wing 28 is lapped over the corresponding front wing 26 and the closure means are used to attach the two. Those skilled in the art will know that the closure means are preferably made adjustable so that the overlap of the rear wing over the front wing can vary. This variance allows the adjustment of the waist size. The reader will observe how the two leg reliefs 12 form leg holes in the state shown in FIG. 2. The user will of course occupy interior 62. The reader will thus understand that the diaper has an inward facing surface directed toward the user and an outward facing surface directed away from the user.

Returning now to FIG. 1, additional features will be described. The outward facing surface of the diaper is covered by a sealing layer of moisture-proof material. This layer is preferably joined to the rest of the diaper by lapping a hem 30 over the inward facing surface and adhering the hem in place (typically using an adhesive). Hem 30 can extend around the entire perimeter. The boundary of the leg relief portions preferably includes an elastic cuff in order to seal against the user's legs.

These previously-described features are conventional in the art. Numerous variations are possible on the general design of these conventional features. As they do not comprise the novel aspects of the present invention, such variations are not of great significance.

The present invention primarily seeks to more effectively handle solid materials. Diaper 10 contains an integral feces receiver 14 for this purpose. Feces receiver 14 is positioned to receive solid waste and contain it so that contact with the user is minimized.

Figure 3:
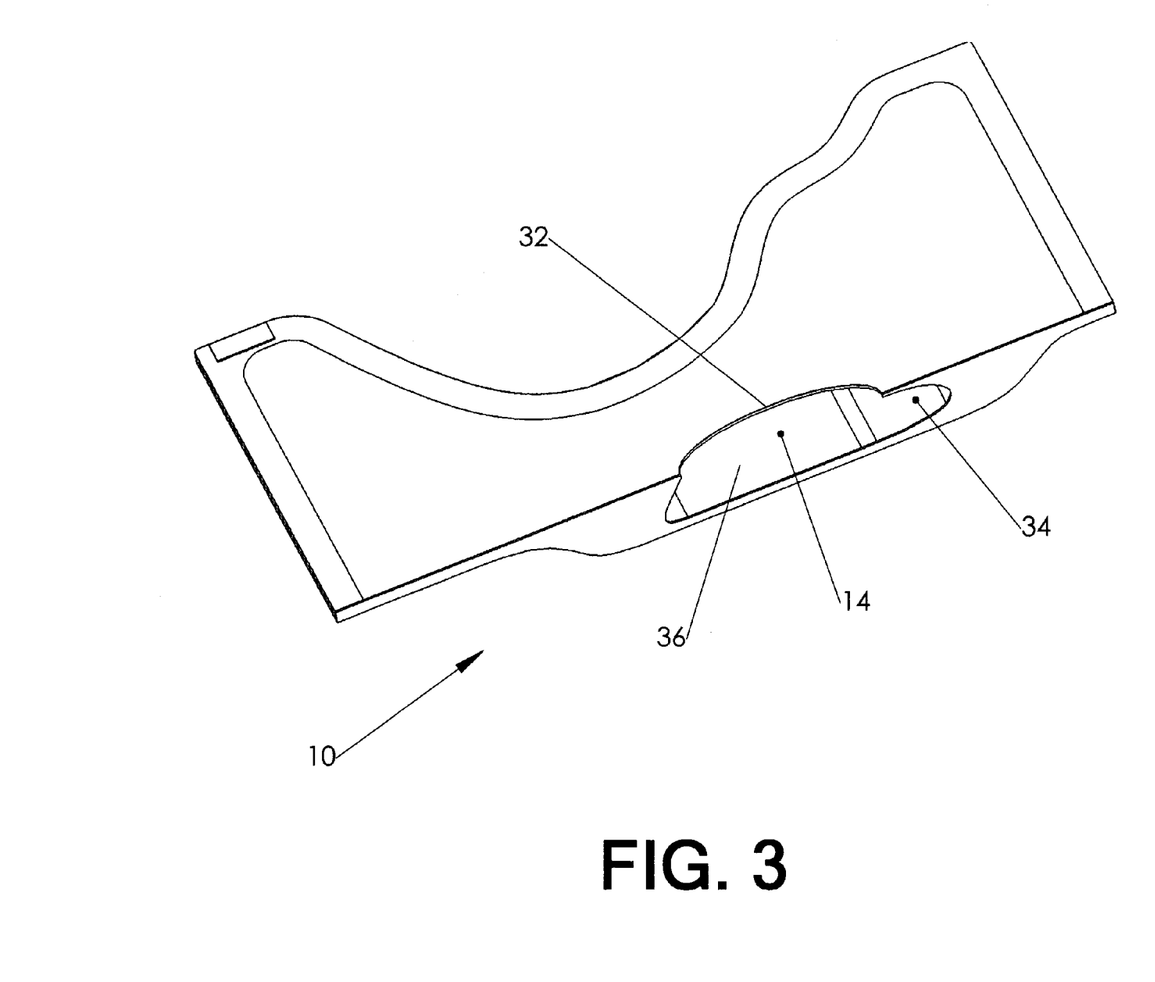
FIG. 3 is a section view, showing details of the receiver.

FIG. 3 shows a section through the diaper's long axis. Feces receiver 14 is connected to the inward facing surface of the diaper by opening 32. The volume of the feces receiver actually lies proximate the outward facing surface, however. The volume is defined by a continuous side wall 64 and bottom wall 36.

Side wall 64 and bottom wall 36 are formed of absorbent material. Of course, beneath bottom wall 36 and outside of side wall 64 lies the sealing layer which covers the entire outside of the diaper. The reader will observe that side wall 64 includes an undercut 34. This undercut extends around substantially all (if not all) of feces receiver 14. The result is that the cross section of the feces receiver increases proceeding from opening 32 toward bottom wall 36.

Figure 4:
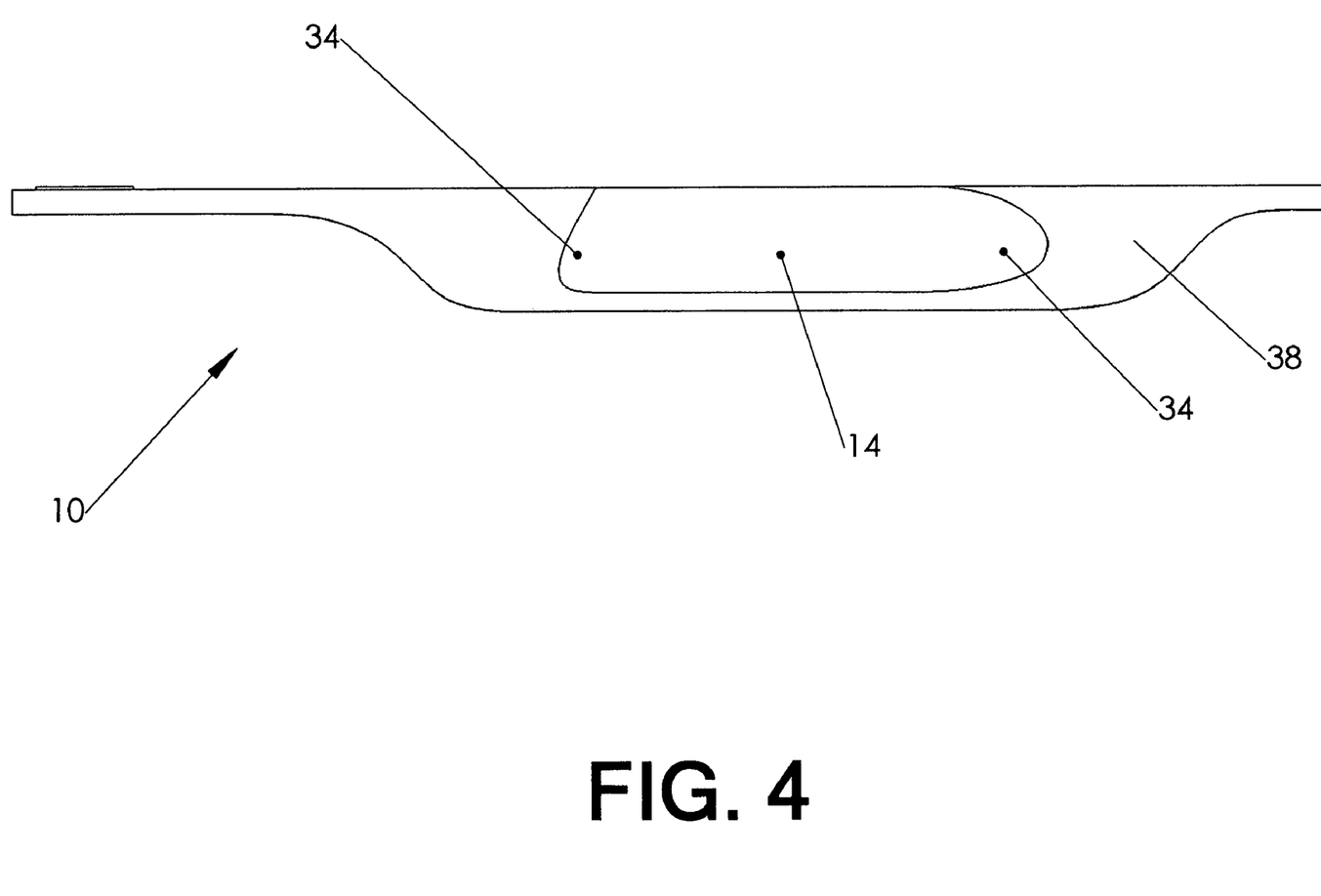
FIG. 4 is a section view, showing details of the receiver.

FIG. 4 shows the same section in an elevation view. The presence of undercut 34 is easy to see in this view. The reader will also observe that the side wall is substantially thickened around the receiver. This added thickness is denoted as support 38.

The diaper is intended to deal with incontinence issues. Those skilled in the art will know that most users suffering from this condition are bedridden most of the time. The user will be wearing the diaper, and a portion of the user's weight will bear upon the lower portions of the diaper. Most such patients will be lying flat in bed, or lying in an inclined bed with the torso being inclined upward between about 10 and 30 degrees. Such an inclined bed may also elevate the legs. The position of the patient may be similar to that of a person sitting in a recliner chair with the chair fully reclined. Such a position puts a portion of the user's weight directly on the tail bone. Feces receiver 14 typically lies just beneath the tail bone when the diaper is worn. Thus, the user's weight may tend to collapse the feces receiver and force any accumulated solids back against the user's skin.

Figure 5:
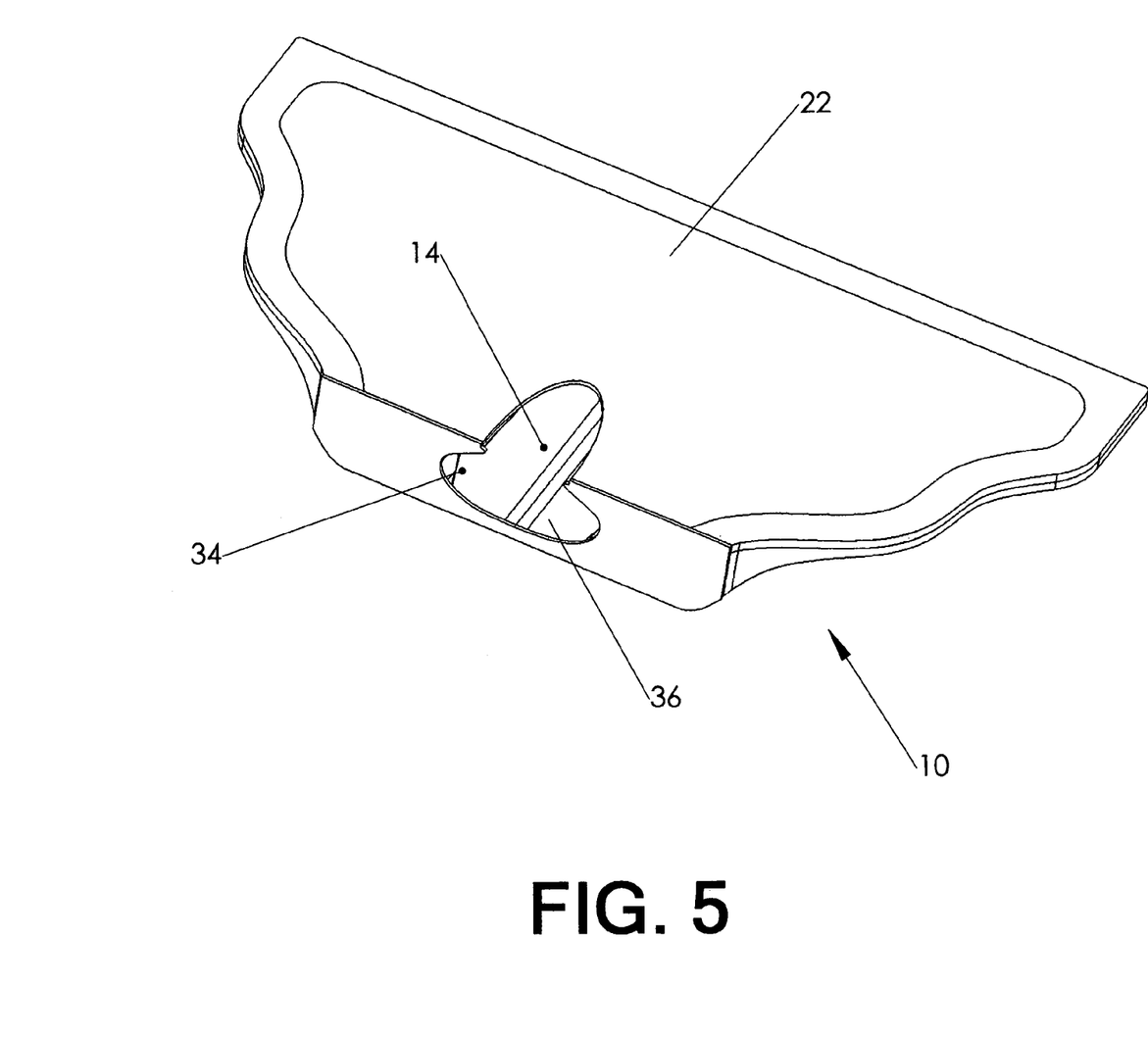
FIG. 5 is a section view, showing details of the receiver.
Figure 6:
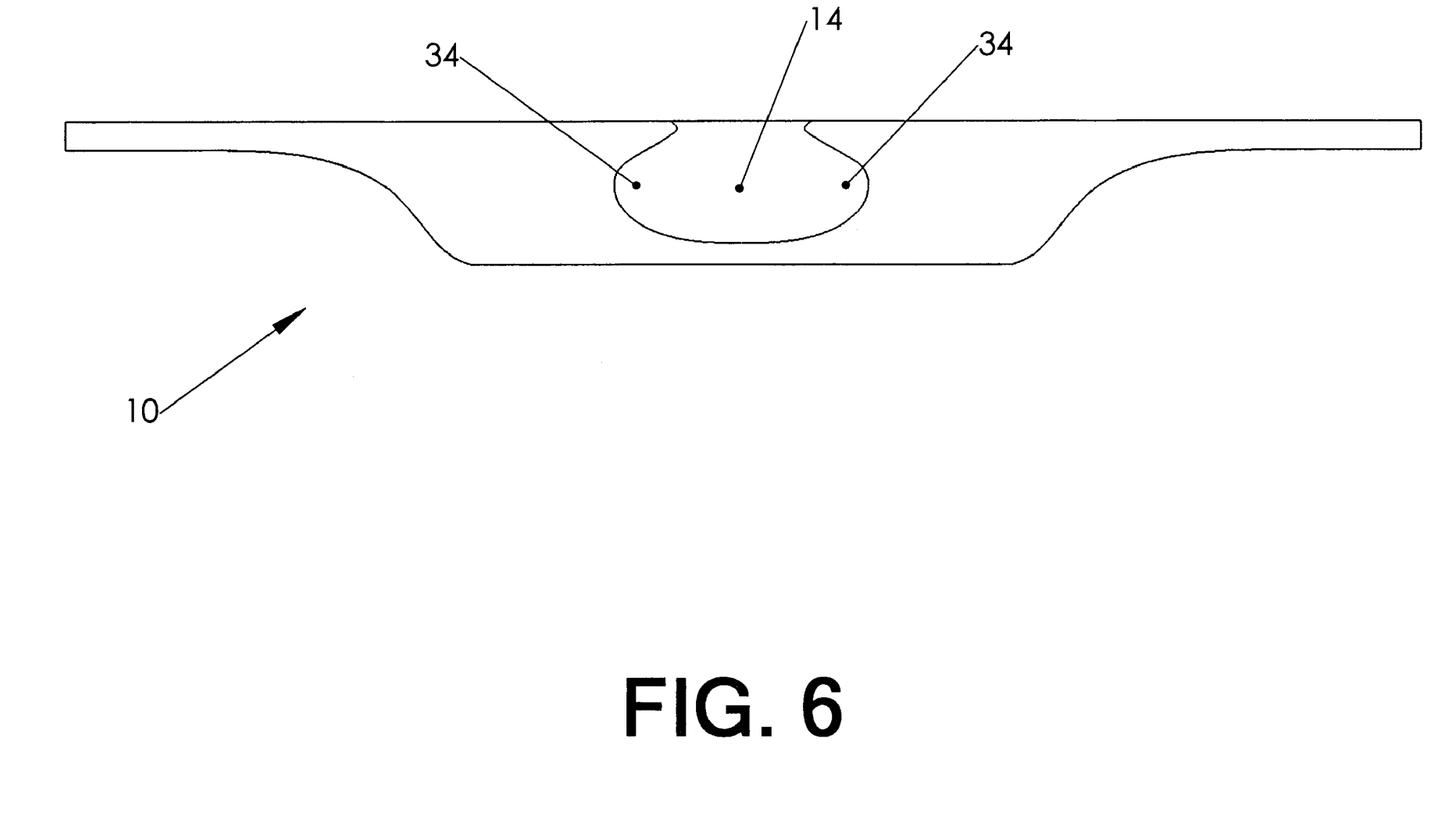
FIG. 6 is a section view, showing details of the receiver.

Support 38 is a thickness of material which is sufficient to resist the collapse of the feces receiver. FIG. 5 shows a transverse section through feces receiver 14. The reader will observe that undercut 34 continues down the side portions of side wall 64. FIG. 6 shows the same section in an elevation view. Support 38 is present around the perimeter of the feces receiver in order to prevent collapse under the user's weight.

The undercut nature of the side wall helps retain the solid waste in the feces receiver. Returning to FIG. 4, those skilled in the art will realize that when the diaper is worn by a patient in bed, the rear portion of the receiver (toward the right in the view) will be lower than the forward portion. The large undercut toward the rear (toward the right in the view) will thereby tend to entrap the solids when they flow downward. In addition, the undercut nature of the side wall means that when the receiver is compressed under the user's weight, the opening tends to close. These features tend to isolate the solid waste from contact with the user's skin.

Figure 7:
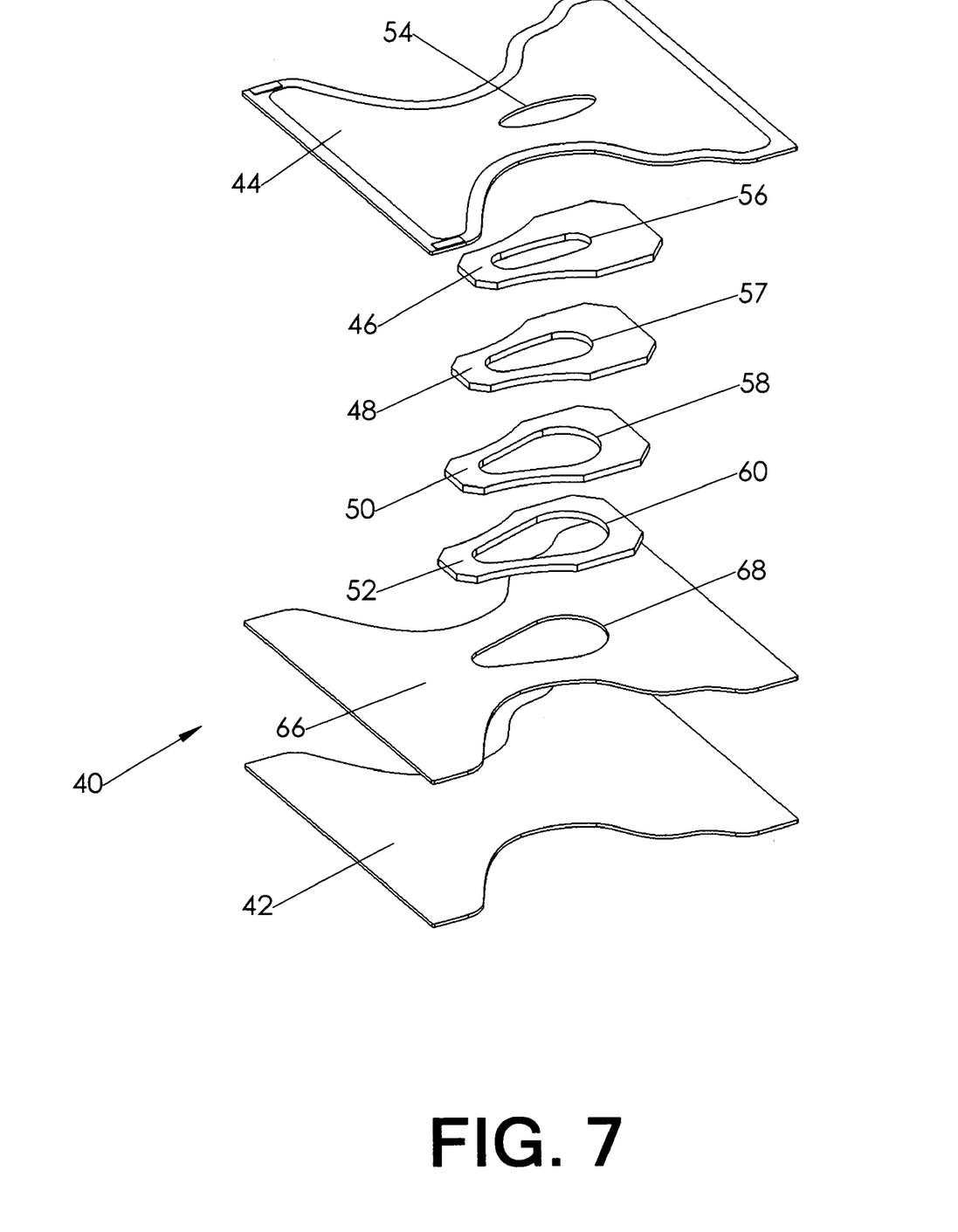
FIG. 7 is an exploded view, showing how the diaper can be made from multiple layers.

The version shown in FIGS. 1-6 contemplates the use of an absorbent material having a varying thickness. The absorbent material can be molded into this shape, then covered by the sealing layer. Alternatively, the diaper can be made as a lamination of multiple layers having approximately the same thickness. FIG. 7 shows the laminated embodiment in an exploded view.

The uppermost component (which will be the portion actually contacting the user when the diaper is worn) is first absorbent layer 44. It is made of absorbent material. It includes first opening 54, which corresponds to opening 32 in the non-laminated embodiment.

The next component is second absorbent layer 46. Second opening 56 forms the upper portion of the side wall defining the feces receiver. Third absorbent layer 48 is next, including third opening 57. This is followed by fourth absorbent layer 50, with fourth opening 58, fifth absorbent layer 52 with fifth opening 60, and lower layer 66 with sixth opening 68. Sealing layer 42 forms the bottom of the diaper. It preferably includes an absorbent layer on its upper surface with a moisture barrier on the bottom.

The layers are stacked together and optionally bonded in place using adhesives or mechanical fastening such as stitching. Although the entire perimeter of each layer can be bonded, this is not strictly necessary for the stability of the stack. Second absorbent layer 46 should be well bonded over most of its surface area to first absorbent layer 44. This need not be the case for all the layers, however.

Figure 7B:
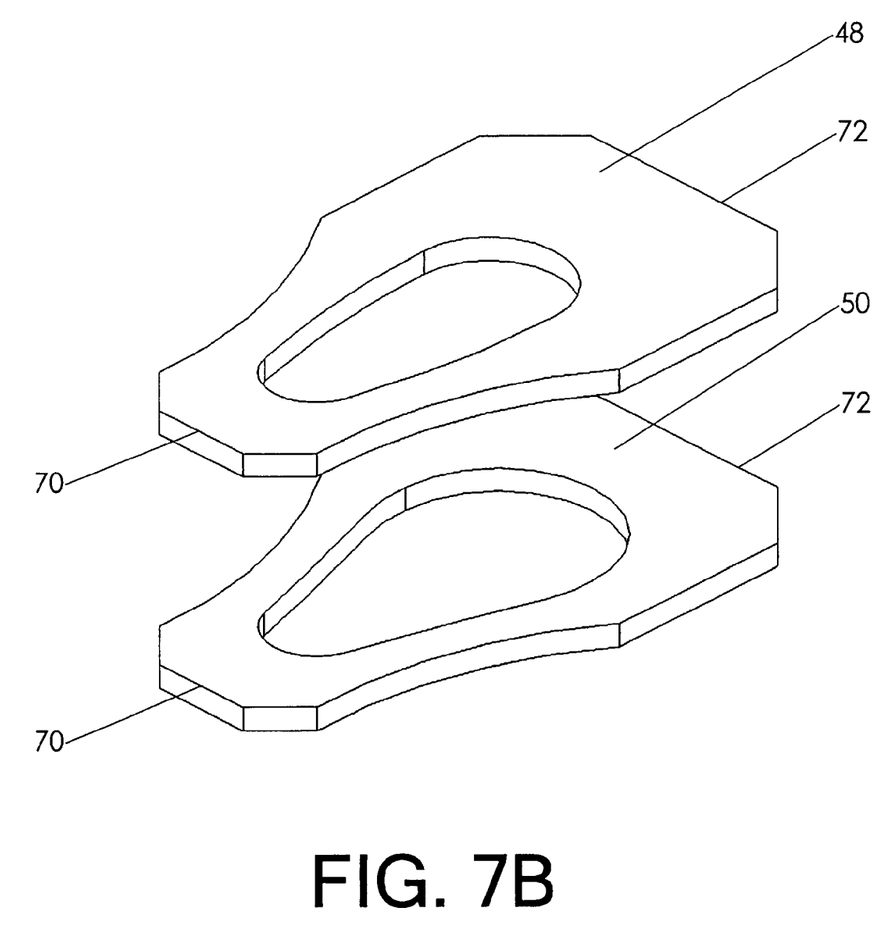
FIG. 7B is a perspective view, showing two layers of the diaper.

FIG. 7B shows third absorbent layer 48 over fourth absorbent layer 50. These may be bonded together only along front edge 70 and rear edge 72. This same front and back bonding can be used on each of the layers descending in the stack until fifth absorbent layer 52 is reached. Fifth absorbent layer 52 should be bonded around the perimeter of fifth opening 60 to lower layer 66. Likewise, lower layer 66 should be bonded around the perimeter of sixth opening 68 to sealing layer 42. This bonding scheme is sufficient to ensure the stability of the stack. Of course, more bonding can be used if desired.

Figure 8:
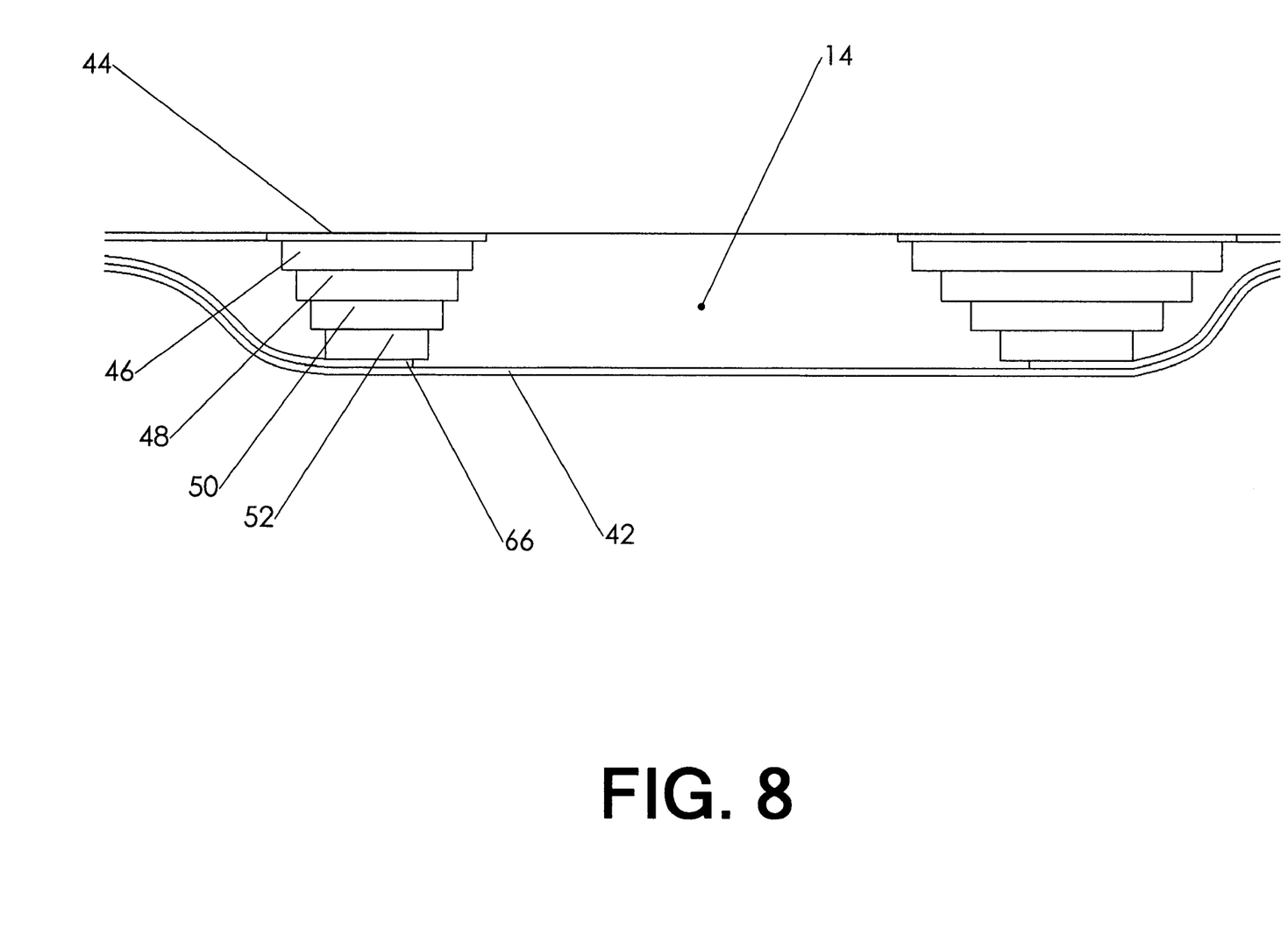
FIG. 8 is a section view, showing how the diaper can be made from multiple layers.

FIG. 8 shows a cross section through the feces receiver in the laminated version, once the layers are bonded together. The reader will observe that the general configuration of the feces receiver is the same, even though the side walls (including the undercut) assume the form of a series of steps rather than a smooth wall. Of course, the holes through the layers can be cut at an angle to avoid the staircase effect if desired. However, there is little if any loss of functionality by the inclusion of the steps.

The use of the sealing layer 42 allows another function of the present invention. The diaper may well entrap a substantial quantity of fecal matter. Disposal of such a used diaper raises concerns. It is desirable, therefore, to expel the fecal matter from the diaper prior to throwing the diaper away.

In order to accomplish this objective, sealing layer 42 can be made detachable from the rest of the diaper. This can be done in a variety of ways, including the use of tearable perforations or a peelable adhesive.

Once the diaper is removed from the wearer, it can be placed over a toilet. The user can then peel sealing layer 42 away, which allows the contents of the feces receiver to spill into the toilet. The emptied diaper can then be thrown away, incinerated, etc.

The size of the diaper has not been specified in this disclosure, since it can be varied to accommodate many different classes of users. As an example, a relatively small version can be made for use with infants. A version of moderate size can be made for use with adolescents or small adults. A large size can be made for use with adults. All these sizes would incorporate the same features.

Although the preceding description contains significant detail, it should not be viewed as limiting the invention but rather as providing examples of the preferred embodiments.

Accordingly, the scope of the invention should be fixed by the following claims rather than by any examples given.

Having described my invention, I claim:

1. A diaper to be worn by a user, comprising:
   a. a first absorbent layer, including
      i. a center portion;
      ii. wherein said center portion has an inward facing surface directed toward said user when said diaper is worn, and an outward facing surface directed away from said user when said diaper is worn;
      iii. a first opening;
   b. a second absorbent layer, lying beneath said first absorbent layer, including a second opening aligned with said first opening which is larger than said first opening;
   c. a third absorbent layer, lying beneath said second absorbent layer, including a third opening aligned with said second opening which is larger than said second opening;
   d. a sealing layer, lying beneath said third absorbent layer;
   e. wherein said first opening, said second opening, said third opening, and said sealing layer combine to define a feces receiver lying proximate said outward facing surface;
   f. wherein the increasing size of said first, second, and third openings define an undercut side wall in said feces receiver; and
   g. wherein said second and third absorbent layers have sufficient strength to prevent the collapse of said feces receiver under the weight of said user.

2. A diaper as recited in claim 1, further comprising a fourth absorbent layer, lying beneath said third absorbent layer and above said sealing layer, including a fourth opening aligned with said third opening which is larger than said third opening.

3. A diaper as recited in claim 2, wherein said sealing layer can be removed in order to empty the contents of said feces receiver.

4. A diaper as recited in claim 2, further comprising a fifth absorbent layer, lying beneath said fourth absorbent layer and above said sealing layer, including a fifth opening aligned with said fourth opening which is larger than said fourth opening.

5. A diaper as recited in claim 4, wherein said sealing layer can be removed in order to empty the contents of said feces receiver.

6. A diaper as recited in claim 1, further comprising:
   a. a rear belt joined to said center portion;
   b. a front belt joined to said center portion;
   c. wherein said rear belt has a first rear wing and a second rear wing;
   d. wherein said rear belt includes closure means located proximate said first rear wing and said second rear wing;
   e. wherein said front belt has a first front wing and a second front wing; and
   f. wherein said front belt includes closure means located proximate said first front wing and said second front wing.

7. A diaper as recited in claim 6, wherein said closure means located proximate said first rear wing, said second rear wing, said first front wing, and said second front wing comprise adhesive strips.

8. A diaper as recited in claim 6, wherein said closure means located proximate said first rear wing, said second rear wing, said first front wing, and said second front wing comprise hook and loop fasteners.

9. A diaper as recited in claim 6, further comprising first and second leg reliefs.

10. A diaper as recited in claim 6, wherein said rear belt includes an elastic portion.

11. A diaper as recited in claim 6, wherein said front belt includes an elastic portion.

12. A diaper as recited in claim 1, wherein said sealing layer can be removed in order to empty the contents of said feces receiver.

* * * * *

UNITED STATES PATENT AND TRADEMARK OFFICE
CERTIFICATE OF CORRECTION

PATENT NO. : 7,160,280 B2  Page 1 of 1
APPLICATION NO. : 10/779451
DATED : January 9, 2007
INVENTOR(S) : Brenda Lee Bailey It is certified that error appears in the above-identified patent and that said Letters Patent is hereby corrected as shown below:

Title Pg. Item (76) Inventors: The correct address is as follows: 455 Wateroak Circle, Panama City Beach, Florida 32408

Signed and Sealed this

Seventeenth Day of April, 2007

JON W. DUDAS
*Director of the United States Patent and Trademark Office*